US008226958B2

(12) United States Patent
Nakashima et al.

(10) Patent No.: US 8,226,958 B2
(45) Date of Patent: Jul. 24, 2012

(54) MODIFIED SEB AND PROPHYLACTICS/REMEDIES FOR IMMUNOPATHY CONTAINING THE SAME

(75) Inventors: Toshihiro Nakashima, Kikuchi (JP); Takumi Sasaki, Kikuchi (JP); Kazuhiko Kimachi, Kikuchi (JP); Shigeki Kuwata, Kikuchi (JP); Tsukasa Nishihara, Kikuchi (JP); Atsuko Sakata, Kumamoto (JP); Masao Ohkuchi, Tokorozawa (JP); Tomoyuki Koshi, Shiki (JP); Toshiyuki Edano, Kawagoe (JP)

(73) Assignees: Juridical Foundation the Chemo-Sero-Therapeutic Research Institute, Kumamoto-Ken (JP); Kowa Company, Ltd., Aichi-Ken (JP)

( * ) Notice: Subject to any disclaimer, the term of this patent is extended or adjusted under 35 U.S.C. 154(b) by 0 days.

(21) Appl. No.: 10/551,263

(22) PCT Filed: Mar. 25, 2004

(86) PCT No.: PCT/JP2004/004184
§ 371 (c)(1),
(2), (4) Date: Sep. 28, 2005

(87) PCT Pub. No.: WO2004/087915
PCT Pub. Date: Oct. 14, 2004

(65) Prior Publication Data

US 2007/0166331 A1 Jul. 19, 2007

(30) Foreign Application Priority Data

Mar. 28, 2003 (JP) ................................ 2003-091819

(51) Int. Cl.

| | |
|---|---|
| ***A61K 39/00*** | (2006.01) |
| ***A61K 39/02*** | (2006.01) |
| ***A61K 39/085*** | (2006.01) |
| ***C07K 1/00*** | (2006.01) |
| ***C07K 14/00*** | (2006.01) |
| ***C07K 17/00*** | (2006.01) |

(52) U.S. Cl. ............... 424/243.1; 424/184.1; 424/185.1; 424/190.1; 424/234.1; 530/350

(58) Field of Classification Search ........................ None
See application file for complete search history.

(56) References Cited

U.S. PATENT DOCUMENTS

| | | | | |
|---|---|---|---|---|
| 6,180,097 | B1 * | 1/2001 | Terman | 424/93.1 |
| 2006/0024322 | A1 | 2/2006 | Sasaki et al. | |

FOREIGN PATENT DOCUMENTS

| | | | | |
|---|---|---|---|---|
| EP | 1 055 429 | A1 | | 2/1999 |
| EP | 1055429 | A1 | * | 11/2000 |
| JP | 09-110704 | | | 4/1997 |
| WO | WO93/14634 | | * | 8/1993 |
| WO | 99/40935 | A1 | | 8/1999 |
| WO | WO 03/002143 | A1 | * | 1/2003 |

OTHER PUBLICATIONS

Nishi et al. The Journal of Immunology, 1997, 1558:247-254.*
Smith et al. Ann Intern Med. 2002; 136:908-922.*
Definition of Immunopathy: http://medical-dictionary.thefreedictionary.com/immunopathy. Retrieved Sep. 12, 2008.*
Llewelyn et al. 2002. The Lancet Infectious Diseases 2: 156-162.*
Watanabe, W. "Pharmacotherapy on juvenile rheumatoid arthritis"; Rheumatism; vol. 36, No. 4, pp. 670-675, 1996.
Ichikawa, Y. et al., "Methotrexate and salazosulfapyridine in the long-term treatment of rheumatoid arthritis"; vol. 35, No. 4, pp. 663-670, 1995.
Kashiwazaki, S. et al., "Prospective clinical study of the combination therapy of auranofin and methotrexate for rheumatoid arthritis- a multi-center study"; Ryumachi, 1996, vol. 36, No. 3, pp. 528-544.
Furutani, T. et al., "Adverse effects of low-dose methotrexate on rheumatoid arthritis", Ryumachi, Oct. 1996, vol. 36, No. 5, pp. 746-752.
Yamamura, Y. et at., "Immunodeficiency due to medicament"; Immunological Science; vol. 9, pp. 285-289, 1984.
Totokawa, S. et al., "Effects of low-dose methotrexate therapy in rheumatoid arthritis: a comparison of three Different dosage regiments"; Ryumachi, Oct. 1997, vol. 37, No. 5, pp. 681-687.
White, J. et al., "The VB-Specific Superantigen Staphylococcal Enterotoxin B: Stimulation of Mature T Cells and Clonal Deletion in Neonatal Mice"; Cell, vol. 56, pp. 27-35, Jan. 13, 1989.
Micusan, V.V. et al., "Superantigens of microbial origin"; Seminars in Immunnology, vol. 5, 1993, pp. 3-11.
Kim, C. et al., "Reduction of Lupus Nephritis in MRL/lpr Mice by a Bacterial Superantigen Treatment"; J. Exp. Med, vol. 174, Dec. 1991, pp. 1431-1437.
Rott, O. et at., "Protection from experimental allergic encephalomyelitis by application of a bacterial antigen"; International Immunology, vol. 4, No. 3, pp. 347-353, 1992.
Kuwahata, M. et al., "Age-related occurrence of inhibitory antibodies to streptococcal pyrogenic superantigens"; Acta Paediatricia Japonica, vol. 38, pp. 1-7, 1996.

(Continued)

*Primary Examiner* — Oluwatosin Ogunbiyi
(74) *Attorney, Agent, or Firm* — Browdy and Neimark, PLLC

(57) ABSTRACT

A novel prophylactic/remedy for immunopathy is provided which is not neutralized by a neutralizing antibody to Staphylococcal enterotoxin B (SEB), known as one of superantigens, and may effectively act as a superantigen. A modified SEB having a reduced reactivity with a neutralizing antibody to SEB (anti-SEB antibody) and a prophylactic/remedy for immunopathy comprising as an active ingredient said modified SEB. The modified SEB of the present invention may be prepared with the evolutionary molecular engineering technique by introducing amino acid substitution in the amino acid sequence of SEB, especially at an epitope recognition site of the anti-SEB antibody in the amino acid sequence of SEB.

4 Claims, 8 Drawing Sheets

OTHER PUBLICATIONS

Origuchi, T. et al., “Increased levels of serum IgM antibody to staphylococcal enterotoxin B in patients with Rheumatoid arthritis”; Annals of the Rheumatic Diseases, vol. 54, pp. 713-720, 1995.

Nishi, J. et al., “B Cell Epitope Mapping of the Bacterial Superantigen Staphylococcal Enterotoxin B”; The Journal of Immunology, 1997, vol. 158, pp. 247-254.

* cited by examiner (A)

(B)

- ◆ N23Y 100 ng/mL
- ■ 42-C-2 100 ng/mL
- ▲ 47-C-7 100 ng/mL
- ● 4-C-1 100 ng/mL
- ■ wild-type SEB 100 ng/mL (A)

(B)

MODIFIED SEB AND PROPHYLACTICS/REMEDIES FOR IMMUNOPATHY CONTAINING THE SAME

TECHNICAL FIELD OF THE INVENTION

The present invention relates to novel prophylactics/remedies for immunopathy. More specifically, the present invention relates to modified forms of Staphylococcal enterotoxin B (hereinafter referred to as "SEB"), known as one of superantigens, and prophylactics/remedies for immunopathy such as rheumatoid arthritis, allergic diseases, etc. comprising as an active ingredient said modified SEB.

BACKGROUND OF THE INVENTION

Autoimmune diseases are classified into two types: organ-nonspecific type autoimmune diseases such as rheumatoid arthritis (hereinafter also referred to as "RA") and organ-specific type autoimmune diseases such as ulcerative colitis. They are induced by T cells responsive to self antigens, said T cells being normally under immunological tolerance, that were activated within self tissues by certain causes to respond to self antigens, leading to continuous inflammatory reactions to thereby damage tissues. In such cases, self antigens are type II collagen that constitutes self joint or main components of the mucous membrane of the intestine, respectively.

The number of patients suffering from these diseases has been slightly increasing year by year but no effective remedies or prophylaxis have been found (Nobuo Watanabe, "Pharmacotherapy on juvenile rheumatoid arthritis", Rheumatism, 1996, Vol. 36, No. 4, p. 670-675). Currently, for treatment of these diseases, there have been employed pharmacotherapy including administ ration of Salazopyrin, 5-aminosalycic acid, azathioprine, 6-MP, tranilast, methotrexate, cyclosporine A, or metronidazole, and administration of an excess amount of 7S-immunoglobulin; surgical therapy such as thymectomy or replacement with artificial joint; or symptomatic therapy such as nutritional therapy (Yoichi Ichikawa et al. "Study on efficacy of long-term administration of methotrexate and salazosulfapyridine on rheumatoid arthritis case" Rheumatism, 1995, Vol. 35, p. 663-670; Sadao Kashiwazaki, "Study on efficacy of combination of auranofin and methotrexate on rheumatoid arthritis", Rheumatism, 1996, Vol. 36, p. 528-544; Takefumi Furutani et al., "Detrimental event in therapy with low dose methotiexate on rheumatoid arthritis", Rheumatism, 1996, Vol. 36, p. 746-752; Nobuo Watanabe, Immunological Science, 1984, Vol. 9, p. 285-289 Ed. By Yuichi Yamamura, Chuzo Kishimoto, Robert A Good, "Immunodeficiency due to medicament; and Shin Totokawa et al., "Study on methotrexate therapy in rheumatoid arthritis: Seeking for strategy of more effective administration", Rheumatism, 1997, Vol. 37, p. 681-687). However, these therapies are not eradicative but rather are disadvantageous in that they may cause severe adverse side effects due to long-term ingestion of medicaments. Thus, it is desired to develop more effective prophylactics/remedies and therapy.

SEB is one of enterotoxins (causative toxins of toxin-type food poisoning) produced by *Staphylococcus aureus*. SEB consists of 239 amino acid residues and its amino acid sequence is also known. The SEB molecule comprises two domains, the first domain consisting of residues 1 to 120, and the second domain consisting of residues 127 to 239. At the N-terminal of SEB, three Regions, Region 1 consisting of residues 9 to 23, Region 2 consisting of residues 41 to 53 and Region 3 consisting of residues 60 to 61, were identified that may affect binding of class II Major Histocompatibility Complex (hereinafter referred to as "MHC") and/or binding of T cell antigen receptor (hereinafter referred to as "TCR").

As is well known, SEB is one of bacterial superantigens (White J. et al., Cell, 1989, Vol. 56, p. 27-35). Normal antigens, being complexed with class II MHC, are recognized by TCR on T cells and this recognition is restricted to a haplotype of class II MHC molecule, called "MHC restriction". On the contrary, superantigens are bound to class II MHC molecule irrespective of haplotype and further to a specific p chain variable region (Vβ chain) of TCR. As a consequence, T cells bound with the superantigen are transiently activated, are promoted to divide and propagate and produce inflammatory cytokines (Micusan V. V. & Thibodean J., Seminars in Immunology, 1993, Vol. 5, p. 3-11).

When a superantigen is intravenously or intraperitoneally administered to newborn mice, a subpopulation of T cells having VβTCR responsive to the superantigen is eliminated so that said mice become non-responsive to said antigen, i.e. immunological tolerance. On the other hand, when SEB is administered to adult mice, the condition where T cells bearing VβTCR that binds to the superantigen become non-responsive to further stimulation with the superantigen, i.e. anergy, is induced, to thereby cause immunological tolerance. Such features of a superantigen are distinct from the normal antigen recognition. With the ability to induce immunological tolerance in T cells bearing the specific VβTCR, SEB is suggested to be applicable for prevention or treatment of certain immunopathy, in particular, type I allergic diseases or autoimmune diseases. Indeed, it is reported that SEB administration to a system of disease model mice allowed for inhibition of onset of said disease.

Kim C. et al. reported that lupus nephritis in MRL/lpr mice, model mice of Systemic lupus erythematosus (hereinafter referred to as "SLE"), could be suppressed by previously administering SEB (Kim C. et al., Journal of Experimental Medicine, 1991, vol. 174, p. 1431-1437). Rott O. et al. also reported that SEB was previously administered to a system of Experimental Allergic Encepharomyelitis (hereinafter referred to as "EAE") to induce immunological tolerance in T cells bearing the VpβTCR responsive to SEB to thereby suppress the disease (Rott O. et al., International and National Immunology, 1992, Vol. 4, No. 3, p. 347-353). These results suggest a possibility that SEB may be used as a vaccine to allow for prevention of specific autoimmune diseases.

However, in these experiments, SEB was administered intravenously or intraperitoneally with a dose of as much as around 100 μg per animal. With such a high dose, an extent of pathogenicity not disregarded will inevitably be introduced to mice and antigenicity and immunogenicity are also problematic. In particular, as described above, a superantigen, when administered at a large amount, will induce transient activation of the subpopulation of T cells or antigen-presenting cells to invite acceleration of inflammatory cytokine production, resulting in the acute inflammatory condition within the living body. Besides, in case of human, Kuwahata et al. reported that an anti-SEB antibody is present in blood from almost 100% of children of more than the school age and an anti-IgA antibody is detected in about 50% of the children from analysis of saliva et al. (M. Kuwahata et al., Acta Pediatrica Japonica, 1996, 38, p. 1-7). Origuchi et al. also demonstrated that a level of IgM-type anti-SEB antibody is significantly high in serum from patients suffering from rheumatism (Origuchi et al., Annals of the Rheumatic Disease 1995, 54, p. 713-720). Moreover, Nishi et al. revealed that a major epitope of an anti-SEB antibody in human serum is located at a C-terminal of SEB and an antibody against said C-terminal region is a neutralizing antibody to SEB (Jun-Ichiro Nishi et al., The journal of Immunology, 1997, 158, p. 247-254). This implies that, when SEB is administered to human, SEB will be neutralized for its biological activity by the antibody and eliminated from the living body. Thus, Nishi et al. constructed a mutant SEB lacking the major epitope at the C-terminal using the genetic engineering technique. However, the thus prepared modified SEB could only be expressed in an insoluble form to hamper thorough assessment and analysis. Also said modified SEB could not cope with stable supply of medicine.

To tackle the various problems in association with administration of a large amount of a superantigen, the present inventors provided a measure for effectively inducing immunological tolerance by orally administering a highly purified SEB in a dose not inducing pathogenicity successively for a long period of time (Japanese Patent Publication No. 110704/1997) and constructed a modified SEB and a derivative thereof through molecular alteration of SEB in which inherent toxicity of SEB is reduced while its preventive/therapeutic effect for immunopathy is maintained to prove utility of SEB (WO99/40935).

DISCLOSURE OF THE INVENTION

Technical Problem to be Solved by the Invention

As described above, there is a problem that, when SEB in a natural form is administered to human, SEB will be neutralized for its biological activity by the anti-SEB antibody occurring in the living body which ultimately eliminates SEB from the living body and hence a desired effect of SEB is not expected. Thus, a mutant SEB lacking the major epitope at the C-terminal has been constructed using the genetic engineering technique but the thus prepared modified SEB could only be expressed in an insoluble form to hamper thorough assessment and analysis and could not cope with stable supply of medicine.

Means for Solving the Problems

In order to solve the above problem relating to antigenicity of SEB, the present inventors have studied using the evolutionary molecular engineering technique. As a consequence, by introducing amino acid substitution into naturally occurring SEB or the known modified SEBs and performing screening among the resulting modified SEBs, the present inventors could successfully prepare a modified SEB that has a reduced binding to the anti-SEB neutralizing antibody and is capable of being expressed in a soluble form in *E. coli* to be maintained stably in an aqueous solution and that retains the therapeutic effect to immunopathy equivalent to that of naturally occurring SEB.

The present invention provides for a modified SEB that has a reduced binding to a neutralizing antibody to Staphylococcal enterotoxin B (SEB) (anti-SEB antibody).

More Efficacious Effects than Prior Art

The epitope-modified SEBs of the present invention were demonstrated to have a reduced reactivity with a neutralizing antibody to SEB and to have an activity to ameliorate the symptoms of CIA (collagen-induced arthritis) equivalent to that of N23Y [a mutant in which asparagine residue at 23-position in SEB is substituted with tyrosine; WO99/40935 (PCT/JP99/00638)]. These epitope-modified SEBs are capable of being expressed and secreted in a soluble form and expected for use as efficacious prophylactics/remedies for immunopathy such as rheumatoid arthritis, allergic diseases, and the like.

BEST MODE FOR CARRYING OUT THE INVENTION

Figure 1:
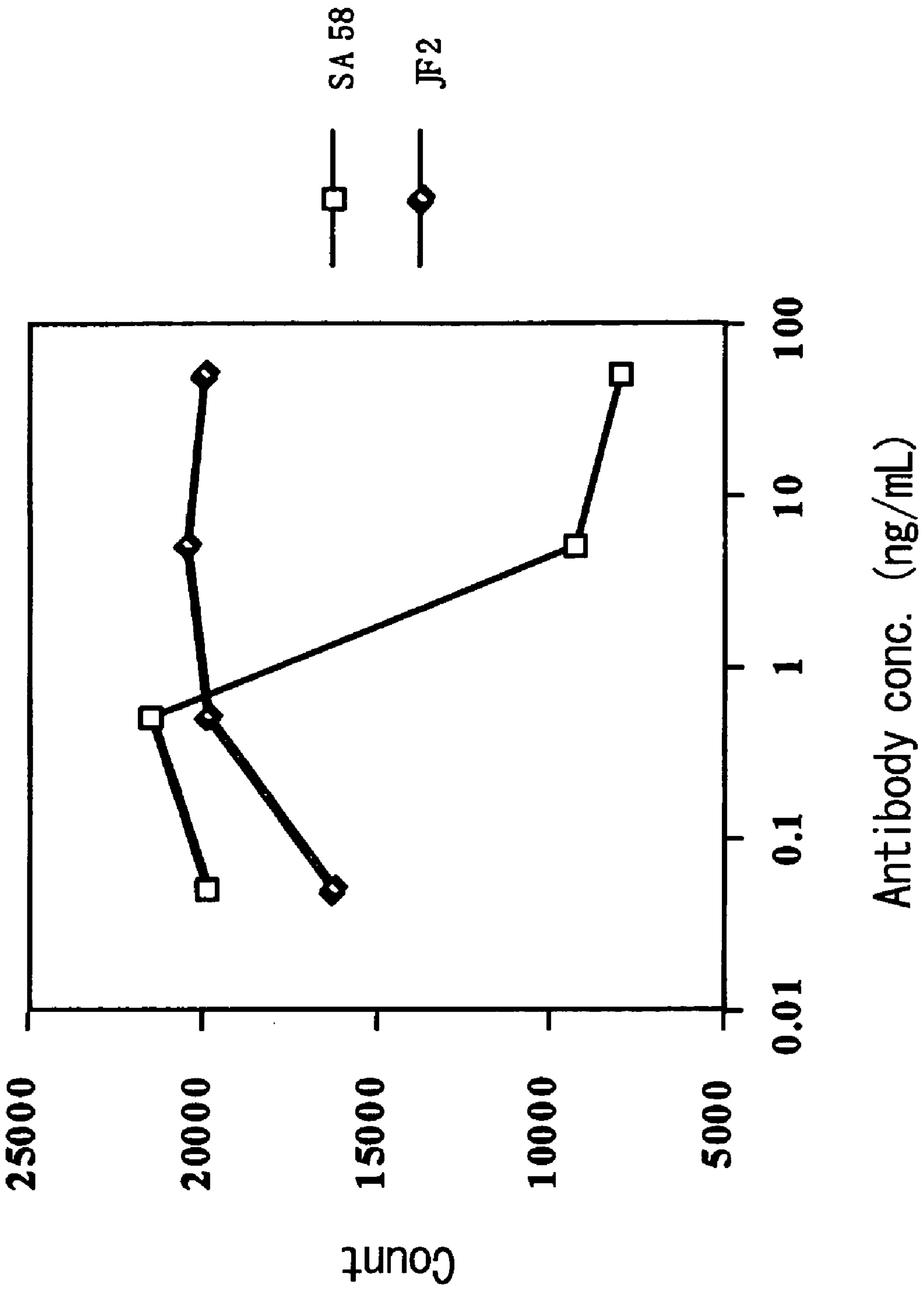
FIG. 1 shows the results of inhibition test of human PBMC (peripheral blood mononuclear cells) activation by SEB using anti-SEB neutralizing monoclonal antibody SA58-2.

The modified SEBs of the present invention may be obtained by introducing arbitrary amino acid substitution into the amino acid sequence of SEB so that it has a reduced reactivity with an anti-SEB antibody. Such introduction of amino acid substitution may preferably be done at an epitope recognition site of an anti-SEB antibody in the amino acid sequence of SEB.

The most preferable site for amino acid substitution in accordance with the present invention is a region from Lys at 226-position to Lys at 229-position in the amino acid sequence of SEB (SEQ ID NO: 1).

The modified SEBs having a reduced reactivity with an anti-SEB antibody in accordance with the present invention include those having any of the following amino acid sequences for the amino acid sequence from the residue at 226-position to the residue at 229-position in the amino acid sequence of SEB:

```
(1) Leu Phe Ala Ala;     (SEQ ID NO: 2)

(2) Ala Thr Thr Gln;     (SEQ ID NO: 3)

(3) Lys Arg Ile Ile.     (SEQ ID NO: 4)
```

The modified SEBs in accordance with the present invention also include those having substitution of Asn at 23-position in the amino acid sequence of SEB with Tyr in combination with the amino acid substitutions as described above.

The present invention further provides for prophylactics/remedies for immunopathy comprising as an active ingredient the modified SEB obtained in accordance with the present invention wherein said prophylactics/remedies has a reduced immunological response to SEB and an inhibitory activity to T cell activation. Immunopathy includes, for instance, rheumatoid arthritis, allergic diseases, and similar diseases.

The "evolutionary molecular engineering technique" used for preparing the modified SEB of the present invention is an approach in which a natural process of evolution (natural selection) in living organisms (it is believed that the probability that an amino acid in a certain protein is substituted with another amino acid is only around once per $10^7$ years) is artificially drastically accelerated in vitro for the purpose of designing useful proteins etc. to allow for evolution (acquisition of novel function, improvement in function, etc.) to occur in several months, which usually takes several ten thousands years in the natural world.

In accordance with the present invention, for preparing the modified SEB having a reduced binding to an anti-SEB neutralizing antibody, amino acid substitution was randomly introduced into the epitope region in SEB recognized by an anti-SEB neutralizing antibody and the resulting modified SEBs were screened for those having a reduced binding to an anti-SEB neutralizing antibody. As described above, it is known that the major epitope of SEB is located at the C-terminal (225 to 234-positions). Within this region, the present inventors had attempted to perform amino acid substitution in four amino acid residues at 226- to 229-positions in the amino acid sequence of SEB. Thus, modified SEBs were prepared and used as a population for selection in vitro in which four amino acid residues at 226- to 229-positions in the amino acid sequence of SEB were arbitrarily substituted with any of the naturally occurring 20 amino acids. From the population, modified SEBs having a reduced binding to an anti-SEB neutralizing antibody were screened. The screened modified SEBs were also confirmed that they are capable of being expressed in s soluble form in *E. coli* to be maintained stably in an aqueous solution and retain the therapeutic effect to immunopathy equivalent to that of naturally occurring SEB.

Specifically, the modified SEBs of the present invention were constructed using the phage display technique as described below.

(1) Construction of Phage Display Library of Wild-Type SEB and Identification of Antigenicity of SEB M13 phages are initially constructed that display wild-type SEB. Using a wild-type SEB expression plasmid incorporated into an expression vector, e.g. pTrc99A (Amersham-Pharmacia), as a template, PCR (polymerase chain reaction) amplification is performed with 5' and 3' primers in which SfiI or NotI recognition sequence is added, respectively. The amplified products are digested with the restriction enzymes SfiI-NotI and incorporated into a plasmid. *E. coli* is then transformed with said plasmid and infected with helper phages to allow for expression of phage particles that display wild-type SEB as a fusion protein with phage g3 protein (SEB-g3 fusion protein). The expression may be confirmed by Western blotting using anti-SEB rabbit polyclonal antibody.

The phages that display SEB are then serially diluted and measured for their reactivity with an anti-SEB neutralizing monoclonal antibody, an anti-SEB antibody derived from human plasma and an anti-Etag antibody in ELISA to determine if SEB is displayed on the surface of the phages with its antigenicity being retained.

(2) Construction of Random Mutant Phage Display Library

Random mutant phage display library is constructed in which random mutations are introduced into SEB or the known modified SEBs at 226- to 231-positions at the C-terminal. Using a plasmid in which SEB or the known modified SEBs are incorporated into an expression vector as a template, PCR is performed to introduce random mutations at 226- to 231-positions. For the known modified SEBs, N23Y [WO99/40935 (PCT/JP99/00638)], for instance, may be used which is a mutant with substitution of the asparagine residue at 23-position of SEB with tyrosine residue.

Mutation may be introduced, for instance, as described below. SEB random genes for arbitrary expression of any of twenty amino acids at 226- to 229-positions are prepared using 5' primer in which SfiI recognition sequence, corresponding to the N-terminal of the full-length SEB, is added and 3' primer in which NotI recognition sequence is added with both primers being incorporated with four repeats of NNK (N is any of A, C, G or T; K is G or T) at the codons corresponding to each amino acid at 226- to 229-positions. After treatment with SfiI/NotI, the SEB random genes are incorporated into plasmids and *E. coli* is transformed with said plasmids to construct a mutant library.

This transformant library is then infected with helper phages to allow for expression of phage particles that display SEB random as a fusion protein with phage g3 protein.

(3) Screening of Modified SEBs Having Low Reactivity with Anti-SEB Neutralizing Antibody The library described above is screened for the reactivity with an anti-SEB neutralizing monoclonal antibody and efficiency of Etag expression. For the anti-SEB neutralizing monoclonal antibody, SA58-2 (manufactured by Juridical Foundation The Chemo-Sero-Therapeutic Research Institute), for instance, may be used as its neutralizing activity has been confirmed. Specifically, in the first step, the random mutant phage display library is reacted with a plate with an immobilized anti-Etag antibody to select phages that express the fusion protein of the modified SEB (g3-Etag-modified SEB) in a soluble form. In the second step, the phages selected in the first step are further reacted with a plate with an immobilized anti-SEB neutralizing monoclonal antibody to thereby recover phages that are incapable of reacting with the antibody. The obtained clones are isolated and analyzed for the sequence of the epitope region where the mutation is introduced, expression of the g3 fusion protein, a site of expression, and reactivity with a human anti-SEB antibody.

(4) Selection and Assessment of Modified SEBs Having Low Reactivity with Anti-SEB Neutralizing Antibody The clones obtained in step (3) above are further screened into several clones with indices of expression in a soluble form, an expression level and reactivity with an anti-SEB antibody. The obtained clones are assessed for their reactivity with an anti-SEB monoclonal antibody and an affinity-purified human anti-SEB antibody in sandwich ELISA.

Finally, the amino acid sequence at the epitope region in the clones having low reactivity is determined.

The present invention is illustrated in more detail by means of the following Examples but should not be construed to be limited thereto.

Example 1

Inhibition of T Cell Activation by SEB with Anti-SEB Antibody

Using SA58-2 antibody (manufactured by Juridical Foundation The Chemo-Sero-Therapeutic Research Institute), a neutralizing monoclonal antibody with specificity against SEB, and JF2 antibody (manufactured by Juridical Foundation The Chemo-Sero-Therapeutic Research Institute) with specificity against Japanese encephalitis virus, SA58-2 antibody was assessed for its ability to neutralize SEB.

Peripheral blood mononuclear cells from healthy adults were inoculated to a 96-well plate at $1\times10^5$ cells/well. The cells were stimulated for three days with SEB (Toxin Technology, Inc.) added to the plate at a concentration of 1 ng/mL and simultaneously SA58-2 and JF2 antibodies were added to the plate at 0.05, 0.5, 5 or 50 ng/mL. Sixteen hours before harvest, the cells were allowed to take up tritium-thymidine (0.5 μCi) for investigating the proliferation-inducing activity.

As a result, the proliferation-stimulating effect by SEB was not inhibited when 50 ng/mL of JF2 antibody was added. On the other hand, when SA58-2 antibody was added, an inhibitory effect of not less than 80% was detected with addition of 5 ng/mL or more (FIG. 1). Thus, it was proved that SA58-2 antibody was a neutralizing antibody that may sufficiently inhibit the lymphocyte-activating capacity of SEB.

Example 2

Reactivity of Modified SEBs with Anti-SEB Antibody (1) Construction of Phage Display Library of Wild-Type SEB and Identification of Antigenicity of SEB Construction of the modified SEBs having low reactivity with an anti-SEB antibody was performed as described below using the evolutionary molecular engineering technique. M13 phages were initially constructed that display wild-type SEB. Using a wild-type SEB expression plasmid (pTrc99A/SEB) incorporated into an expression vector pTrc99A (Amersham-Pharmacia) as a template, PCR (polymerase chain reaction) amplification was performed with 5' and 3' primers in which SfiI or NotI recognition sequence was added, respectively. The amplified products were digested with the restriction enzymes SfiI-NotI and incorporated into pCANTABSE (Pharmacia). This plasmid was referred to as "pCAN/SEB". *E. coli* TG1 was then transformed with pCAN/SEB and infected with helper phages to allow for expression of phage particles that display wild-type SEB as a fusion protein with phage g3 protein (SEB-g3 fusion protein). The expression was confirmed by Western blotting using an anti-SEB rabbit polyclonal antibody.

The phages that display SEB were then serially diluted and measured for their reactivity with the anti-SEB neutralizing monoclonal antibody SA58-2 (manufactured by Juridical Foundation The Chemo-Sero-Therapeutic Research Institute), anti-SEB antibody derived from human plasma and anti-Etag antibody (Amersham-Pharmacia) in ELISA to determine if SEB was displayed on the surface of the phages with its antigenicity being retained. The phages that display SEB were serially diluted by ten-fold starting from $1\times10^{10}$ and added to a 96-well plate. The plate was reacted with the anti-SEB antibodies or the anti-Etag antibody and the reaction was developed with HRP-labeled secondary antibody and absorbance was determined. As a result, it was proved that SEB was expressed and retained on the surface of the phages with its antigenicity equivalent to that of naturally occurring SEB.

(2) Construction of Random Mutant Phage Display Library

Using as a template a plasmid pTrc99A/N23Y in which one of the known modified SEBs, N23Y [a mutant with substitution of the asparagine residue at 23-position of SEB with tyrosine residue: WO99/40935 (PCT/JP99/00638)] was incorporated into pTrc99A, PCR was performed to introduce random mutations at 226- to 229-positions. Mutation was introduced as described below.

N23Y random genes for arbitrary expression of any of twenty amino acids at 226- to 229-positions were prepared using 5' primer in which SfiI recognition sequence, corresponding to the N-terminal of the full-length SEB, was added and 3' primer in which NotI recognition sequence was added with both primers being incorporated with four repeats of NNK (N is any of A, C, G or T; K is G or T) at the codons corresponding to each amino acid at 226- to 229-positions. After treatment with SfiI/NotI, the N23Y random genes were incorporated into pCANTAB5E. This plasmid was referred to as "pCAN/N23Yrandom". *E. coli* TG1 was transformed with pCAN/N23Yrandom to thereby construct a library comprising $1.88\times10^5$ mutants.

This transformant library was then infected with helper phages to allow for expression of phage particles that displayed N23Y random as a fusion protein with phage g3 protein. Reactivity of the phage library with anti-Etag antibody, SA58-2 antibody, and affinity-purified human anti-SEB antibody was analyzed in ELISA. As a result, it was confirmed that a rate of display on the phage of N23Y random was only 1/20 of that of wild-type SEB but its reactivity with SA58-2 antibody and with the affinity-purified human anti-SEB antibody was much reduced, i.e. as low as 1/200 or less of that of wild-type SEB. Accordingly, it was estimated that the reactivity of N23Y random consisting of the library with each of the antibodies was reduced by about 1/10 on an average as compared to that of wild-type SEB, which implied that there were indeed present in this library the sequences having low reactivity with these anti-SEB antibodies.

(3) Screening of Modified SEBs Having Low Reactivity with Anti-SEB Neutralizing Antibody The library described above was screened thrice for the reactivity with SA58-2, i.e. the anti-SEB neutralizing monoclonal antibody with its neutralizing activity being confirmed, and efficiency of Etag expression. Thus, in the first step, the random mutant phage display library was reacted with a plate with an immobilized anti-Etag antibody to select phages that express the fusion protein of the modified SEB (g3-Etag-modified SEB) in a soluble form. In the second step, the phages selected in the first step were further reacted with a plate with the immobilized anti-SEB neutralizing monoclonal antibody SA58-2 to thereby recover phages that were incapable of reacting with the antibody. Among these, 48 clones were arbitrarily isolated and analyzed for the sequence of the epitope region where the mutation was introduced, expression of the g3 fusion protein, a site of expression, and reactivity with a human anti-SEB antibody.

As a result, 30 among these 48 clones were expressed as a fusion protein with g3 and 21 among these 30 clones were capable of being expressed in a culture supernatant. Among these 21 clones, 10 clones were evidently reactive with a human anti-SEB antibody while the remaining 11 clones exhibited extremely lowered reactivity.

(4) Selection and Assessment of Modified SEBs Having Low Reactivity with Anti-SEB Neutralizing Antibody Analysis was further continued for the clones with indices of expression in a soluble form, an expression level and reactivity with anti-SEB antibody to select eight clones; 4-C1, 4-C3, 42-C2, 42-C3, 47-C3, 47-C7, 48-C1 and 48-C4. These clones were assessed for their reactivity with SA58-2 antibody and an affinity-purified human anti-SEB antibody in sandwich ELISA.

Figure 2:
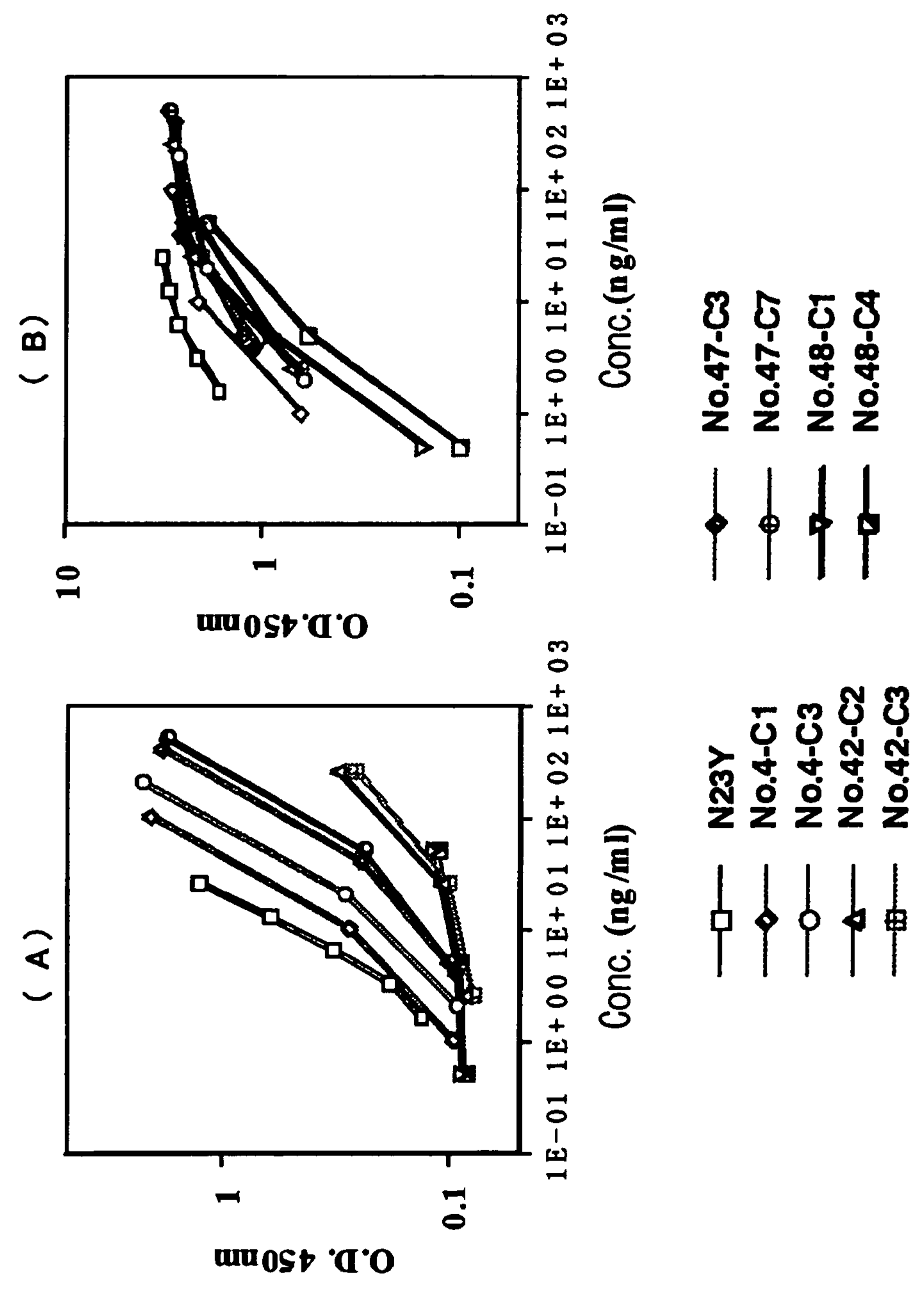
FIG. 2 shows reactivity of the epitope-modified SEBs of the present invention with (A) anti-SEB neutralizing monoclonal antibody SA58-2, or (B) human anti-SEB antibody.

The reactivity of these clones with both antibodies was assessed, taken together with their expression level. As a result, the reactivity was reduced in all of these clones (FIG. 2). In particular, the reactivity with the neutralizing antibody SA58-2 was reduced by about 1/30 to 1/50 in the clones 42-C2, 48-C1 and 48-C4, by about 1/8 in 47-C7, and by about 1/2 in 4-C1, as compared to N23Y used as a template (Table 1). As for the reactivity with the purified human anti-SEB antibody, it was reduced by about 1/8 in 42-C2, 48-C1, 48-C4 and 47-C7, and by about 1/2 to 1/4 in 4-C1 (Table 1). For these clones in which their reactivity with these anti-SEB antibodies was assessed, each of the amino acid sequences at the epitope region was also determined and shown in Table 1.

By assessing the reactivity as described above as a whole, it was determined that 42-C2, 47-C7 and 4-C1 were used in the subsequent experiments. These modified SEBs, obtained with N23Y as a template, are hereinafter collectively referred to as "epitope-modified SEBs".

TABLE 1

Reduced reactivity of epitope-modified SEBs with anti-SEB antibody

| Clone Nos. | Sequence of epitope region | Reactivity with anti-SEB mAb | Reactivity with human anti-SEB Ab |
|---|---|---|---|
| N23Y | SKDVKIEVYL (SEQ ID NO: 5) | 1 | 1 |
| 42-C2 | SLFAAIEVYL (SEQ ID NO: 6) | 1/50 | 1/8 |
| 47-C7 | SATTQIEVYL (SEQ ID NO: 7) | 1/8 | 1/8 |
| 4-C1 | SKRIIIEVYL (SEQ ID NO: 8) | 1/2 | 1/2 to 1/4 |
| 48-C4 | SPQPDIEVYL (SEQ ID NO: 9) | 1/30 | 1/8 |

Example 3

Analysis of Biological Activity of Epitope-Modified SEBs to Peripheral Blood Mononuclear Cell (1) Assessment of Epitope-Modified SEBs for their Proliferation-Inducing or Blast Formation-Inducing Activity Peripheral blood mononuclear cells (hereinafter also referred to as "PBMC") from healthy adults were inoculated to a 96-well plate at $1\times10^5$ cells/well. SEB, N23Y and the epitope-modified SEBs were added to the plate at a concentration of 0.01, 1, 100 and 1000 ng/mL to stimulate the cells for three days. Sixteen hours before harvest, the cells were allowed to take up tritium-thymidine (0.5 μCi) for investigating the proliferation-inducing activity. Also, the above PBMC were cultured in the presence of the modified SEBs at the same concentration for a medium period of time (6 days) to investigate an extent of blast formation of T cells by FSC/SSC analysis of flow cytometry (hereinafter also referred to as "FACS").

Figure 3:
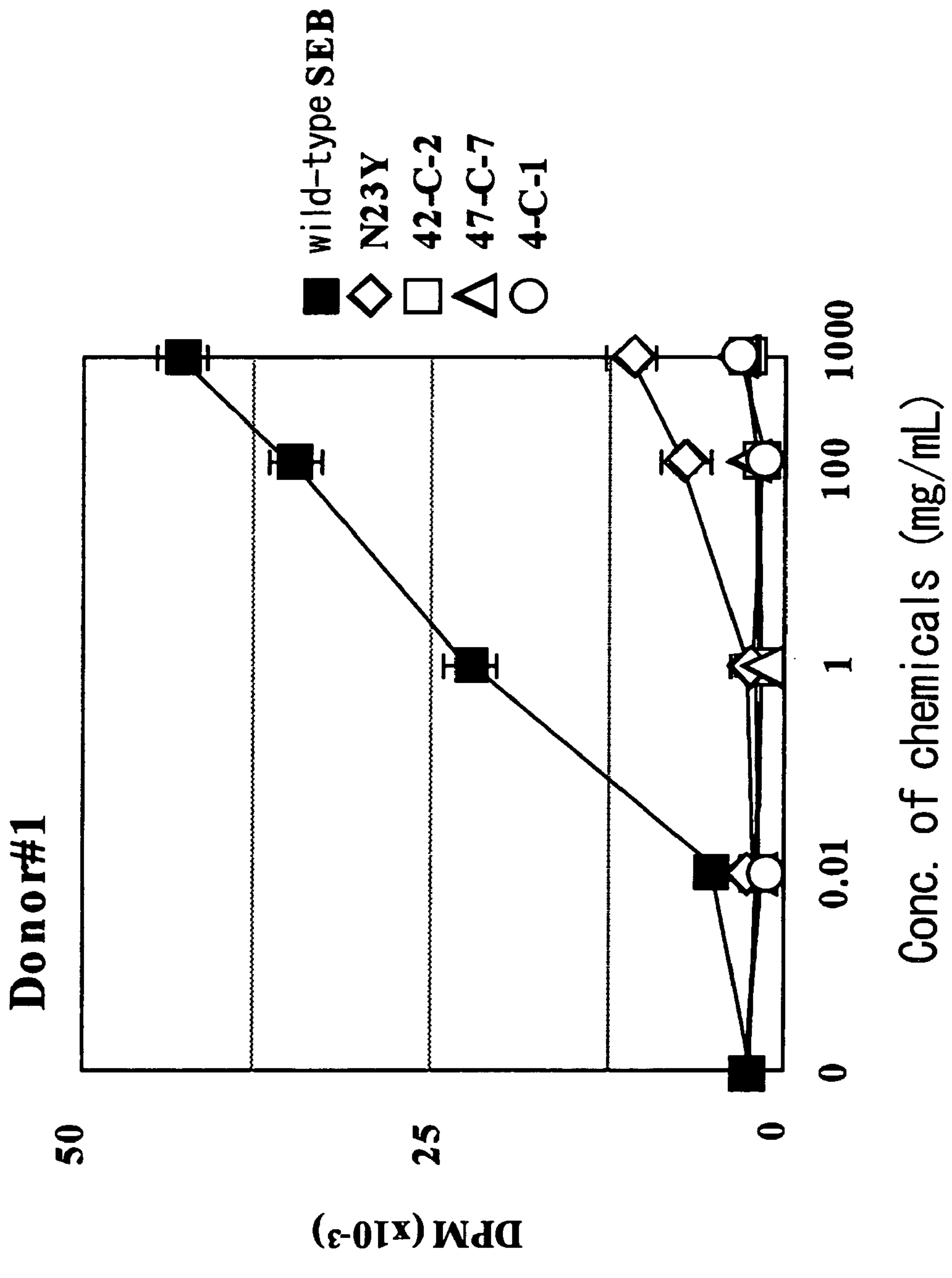
FIG. 3 shows the results of measurement of proliferative response of cells with counts of tritium-thymidine after stimulation of human PBMC with the epitope-modified SEBs of the present invention for three days.
Figure 4:
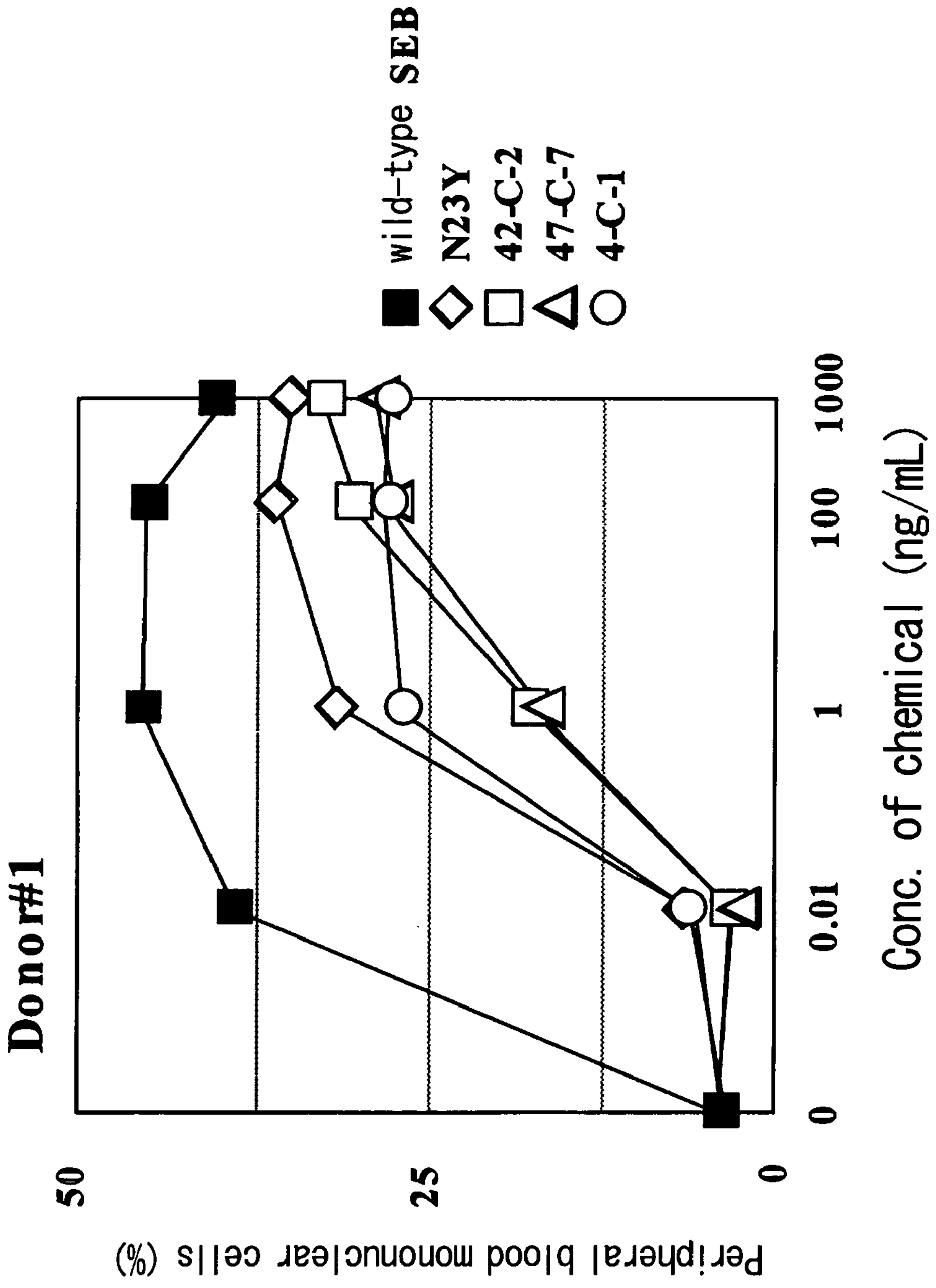
FIG. 4 shows a ratio of blast formation (%) as a result of measurement of blastogenic transformation reaction of cells through flow cytometry after stimulation of human PBMC with the epitope-modified SEBs of the present invention for six days.

As a result, SEB exhibited a potent proliferation-inducing activity to PBMC at 0.01 ng/mL or more in a concentration dependent manner. Typical examples are shown in FIG. 3. N23Y had an extremely lower proliferation-inducing activity than SEB in which an uptake of tritium-thymidine began to be detected at 100 ng/mL or more and was counted as low as about 1/10 of that of SEB even at 1000 ng/mL. The epitope-modified SEBs had a further lowered proliferation-inducing activity (FIG. 3). As for the blast formation-inducing activity, N23Y induced significant blast formation to 10-30% of the cells at 1 ng/mL or more while 42-C2 and 47-C7 had about 1/10 of the inducing activity shown by N23Y. 4-C1 exhibited the activity almost equivalent to that of N23Y (FIG. 3). These results revealed that the epitope-modified SEBs, even if mutation has been introduced into the epitope region, had the biological activity roughly equivalent to N23Y with respect to the proliferation-inducing or blast formation-inducing activity to PBMC in vitro.

(2) Assessment of Epitope-Modified SEBs for their Cytokine-Inducing Activity

PBMC from healthy adults were inoculated to a 24-well plate at $1\times10^6$ cells/well. SEB, N23Y and the epitope-modified SEBs were added to the plate at a concentration of 0.01, 1, 100 and 1000 ng/mL to stimulate the cells for two days and a culture supernatant was collected. The culture supernatant was measured for production of various cytokines (TNF-α, IL-1 β, IL-6, IL-8, IL-12, IFN-γ, IL-Ira, IL-4, IL-10, GM-CSF) with ELISA kit (CytoSets, CytoFix, Asahi Techno Glass Corporation).

As a result, the epitope-modified SEBs like N23Y had a lower activity to produce cytokines than SEB with a similar cytokine-inducing pattern to that of N23Y.

Figure 5:
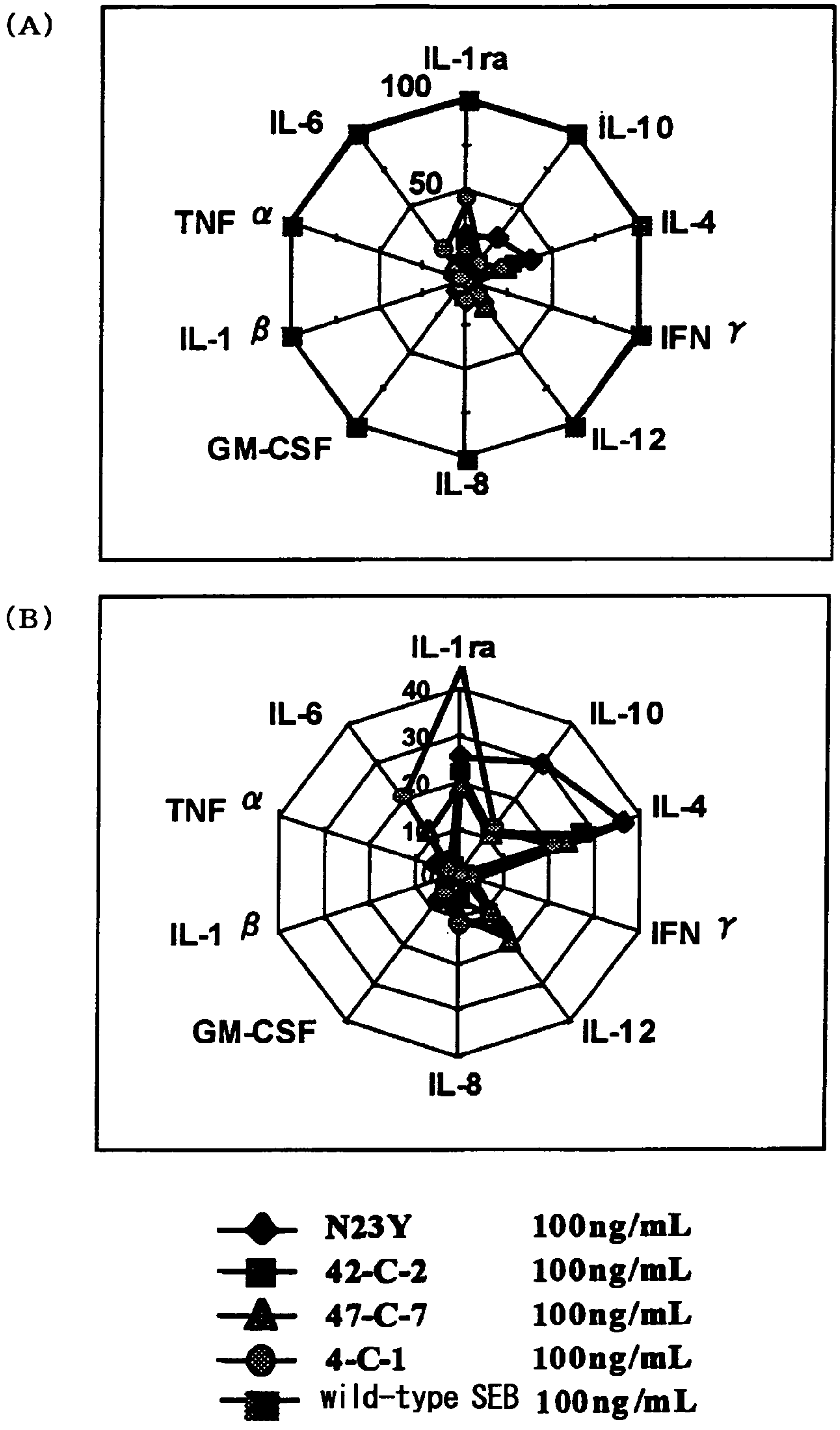
FIG. 5 shows (B) the results obtained by measurement of various cytokines secreted into culture supernatant with ELISA after stimulation of human PBMC with the epitope-modified SEBs of the present invention for two days, and (A) relative values of said measurement as compared to wild-type SEB.

Specifically, they produced inhibitory cytokines such as IL-1ra, IL-10 and IL-4 at a relatively significantly higher level than SEB while they induced inflammatory cytokines such as IL-1β, IL-6, TNF-α, IL-12, GM-CSF and IFN-γ at a relatively lower level than SEB. FIG. 5 shows a relative activity of the epitope-modified SEBs (100 ng/mL) as compared to SEB with the cytokine-inducing activity of SEB at 100 ng/mL being 100%. The epitope-modified SEBs had the biological activity equivalent to that of N23Y with respect to the cytokine-inducing activity to PBMC in vitro.

Besides, since N23Y and the epitope-modified SEBs exhibited a remarkably restricted induction of IFN-γ but a relatively higher production of the inhibitory cytokines IL- and IL-10 as compared to SEB as clearly shown in the results of FIG. 5, it was supposed that the modified SEBs had an activity to shift T populations from Th1 to Th2.

Example 4

(1) Assessment of Epitope-Modified SEBs in Mouse Arthritis Model

Efficacy of N23Y and the epitope-modified SEBs was assessed in mouse collagen-induced arthritis (CIA) model. DBA/1J male mice of 7 weeks old were sensitized with 100 μg/mouse of bovine type II collagen at the root of tail using Freund's complete adjuvant (FCA). After 3 weeks, the mice received booster administration of the same antigen to induce arthritis. One week after the booster administration, each mouse was observed for their limbs and severity of arthritis was scored. Scoring was made for each limb with the following criteria: no onset of disease: 0; swelling in one finger: 1; swelling in two to four fingers or swelling in the instep of limb: 2; swelling in all the fingers or severe swelling: 3. A total score of the four limbs was calculated (maximum 12) and was used as an arthritis score of mouse. A group of mice with slight arthritis having arthritis score of 1 to 4 was selected and orally administered with the chemical. The chemical was administered using a probe at 10 μg/mouse every day for four weeks. After initiation of the chemical administration, mice were scored twice a week and severity of arthritis was observed. After the administration was completed, the joints of the four limbs were photographed with soft X-ray and severity of erosion in bone was scored so as to assess the activity to bone destruction.

Figure 6:
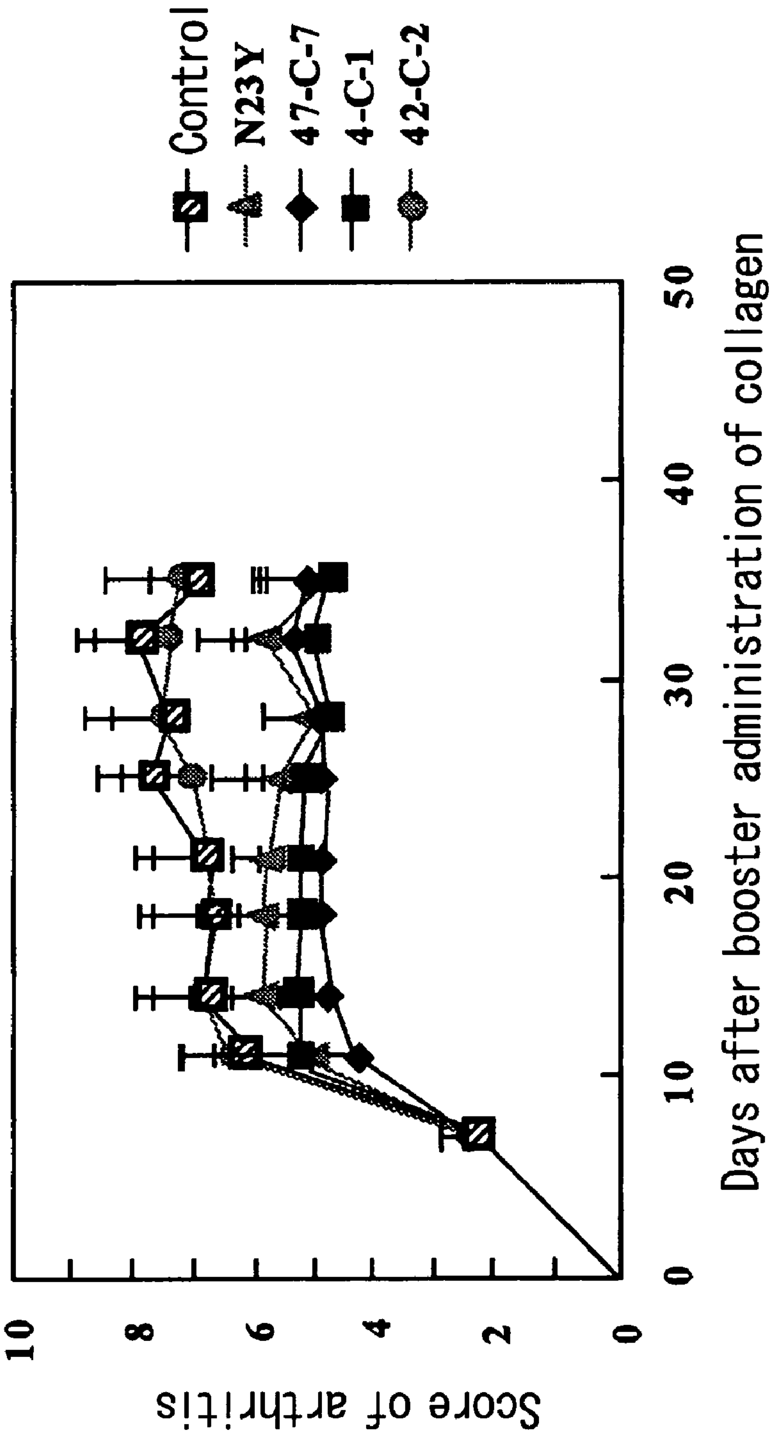
FIG. 6 shows the results of assessment of the epitope-modified SEBs of the present invention for inhibition in swelling of limbs in mouse collagen-induced arthritis (CIA) model.
Figure 7:
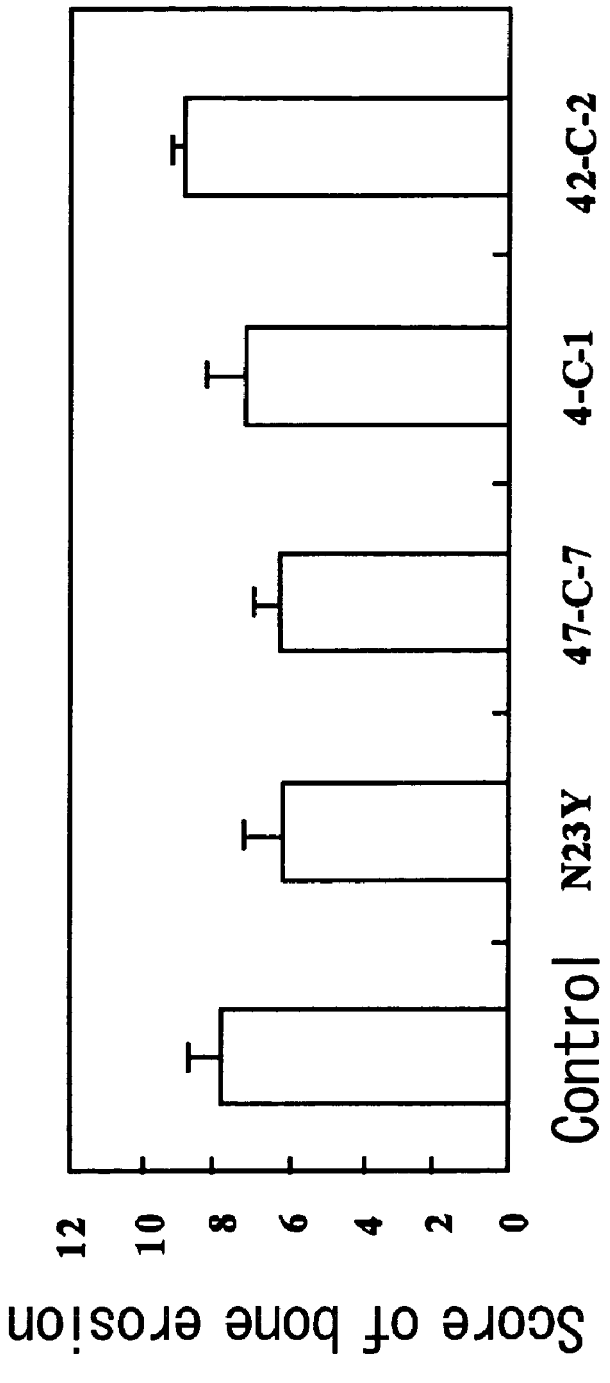
FIG. 7 shows the results of assessment of the epitope-modified SEBs of the present invention for inhibition in bone destruction in mouse collagen-induced arthritis model.

As a result, the epitope-modified SEBs, 4-C1 and 47-C7, significantly inhibited the symptoms of arthritis as compared to the control group where saline was administered. In 42-C2, no inhibitory activity was seen (FIG. 6). In case of 47-C7 and 4-C1, the activity to inhibit bone destruction was also observed (FIG. 7).

(2) Induction of Anti-SEB Antibody by Administration of Epitope-Modified SEBs

Figure 8:
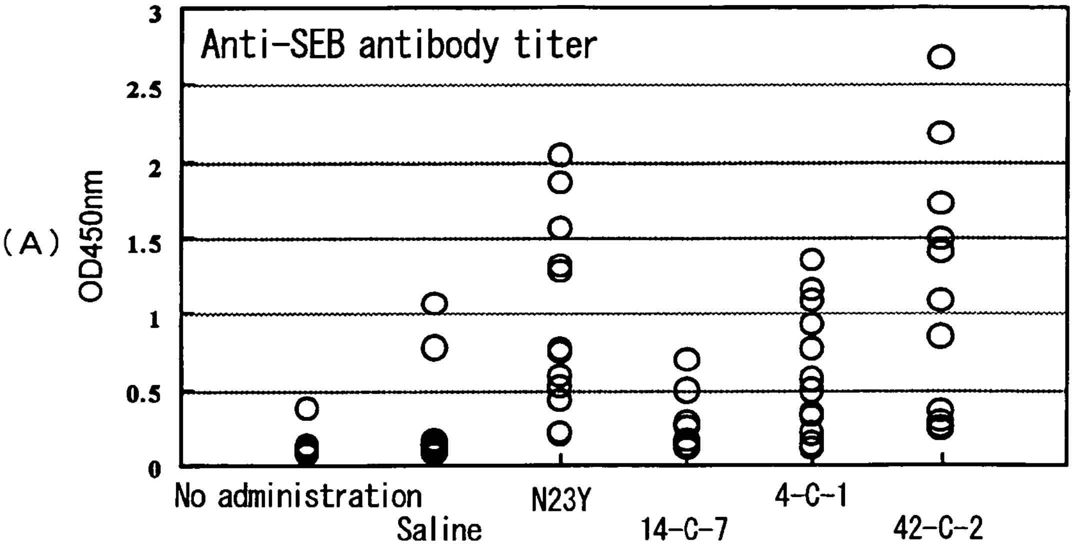
FIG. 8 shows the measurements (absorbance at 450 nm) of (A) anti-SEB antibody titer and (B) anti-47-C7 antibody titer in blood of mice when the epitope-modified SEBs of the present invention are orally administered.
Figure 8:
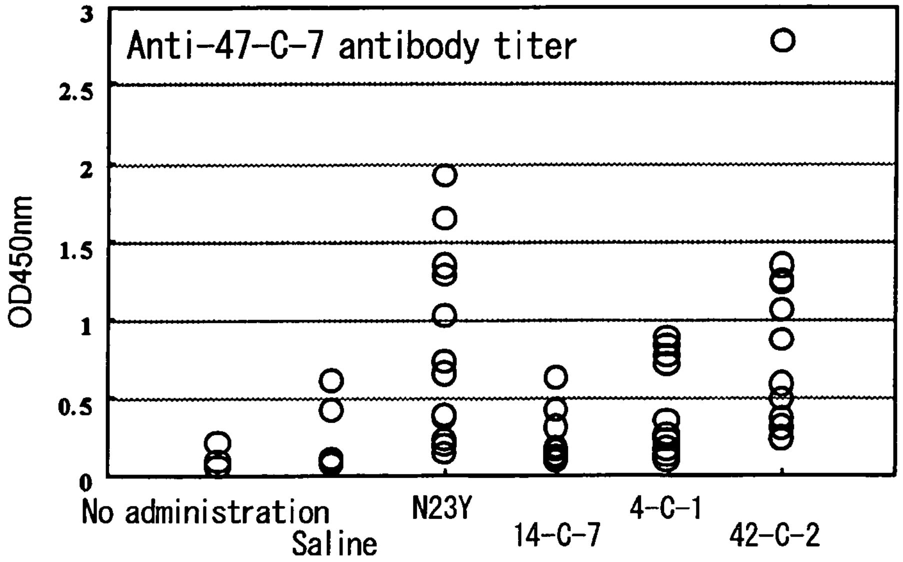

After completion of the tests, whole blood was taken out and a titer of anti-SEB antibody in blood was measured by ELISA. As a result, the group of 47-C7 administration exhibited the titer equivalent to that of the group of no chemical administration or the control group of saline administration and hence had a reduced immunogenicity (FIG. 8 (A)). In addition, the modified SEB, 47-C7, was also less inclined to induce an antibody to this protein per se and hence it was assumed that the possibility was low that the modified epitope sequence became another antigenic epitope (FIG. 8 (B)).

The invention claimed is:

1. A modified Staphylococcal enterotoxin B (SEB) having a reduced reactivity with a neutralizing antibody to SEB (anti-SEB antibody) and having an inhibitory activity to rheumatoid arthritis, wherein the amino acid sequence from residue position 226 to residue position 229 in the amino acid sequence of SEB as shown in SEQ ID NO:1 is Ala Thr Thr Gln and wherein Asn at residue position 23 of SEQ ID NO: 1 is substituted with Tyr.

2. A modified Staphylococcal enterotoxin B (SEB) having a reduced reactivity with a neutralizing antibody to SEB (anti-SEB antibody) and having an inhibitory activity to rheumatoid arthritis, wherein the amino acid sequence from residue position 226 to residue position 229 in the amino acid sequence of SEB as shown in SEQ ID NO:1 is Lys Arg Ile Ile and wherein Asn at residue position 23 of SEQ ID NO: 1 is substituted with Tyr.

3. A modified Staphylococcal enterotoxin B (SEB), having a reduced reactivity with a neutralizing antibody to SEB (anti-SEB antibody), and capable of being expressed in a soluble form in *Escherichia coli* so as to be maintained stably in an aqueous solution and which modified SEB retains a therapeutic effect to rheumatoid arthritis, wherein the reactivity with anti-SEB antibody is reduced as a result of amino acid substitution at residue positions 226 to 229 of SEQ ID NO:1, with the amino acid sequence at residue positions 226 to 229 of SEQ ID NO:1 being substituted with Ala Thr Thr Gln, respectively, or substituted with Lys Arg Ile Ile, respectively, and wherein Asn at residue position 23 of SEQ ID NO:1 is substituted with Tyr.

4. In a method for the treatment of rheumatoid arthritis comprising administration to a patient in need thereof an effective amount of a treatment agent, the improvement wherein the treatment agent comprises the modified SEB of claim 3.

* * * * *

```
                         SEQUENCE LISTING

<160> NUMBER OF SEQ ID NOS: 9

<210> SEQ ID NO 1
<211> LENGTH: 239
<212> TYPE: PRT
<213> ORGANISM: Staphylococcus aureus

<400> SEQUENCE: 1

Glu Ser Gln Pro Asp Pro Lys Pro Asp Glu Leu His Lys Ser Ser Lys
  1               5                  10                  15

Phe Thr Gly Leu Met Glu Asn Met Lys Val Leu Tyr Asp Asp Asn His
             20                  25                  30

Val Ser Ala Ile Asn Val Lys Ser Ile Asp Gln Phe Leu Tyr Phe Asp
         35                  40                  45

Leu Ile Tyr Ser Ile Lys Asp Thr Lys Leu Gly Asn Tyr Asp Asn Val
     50                  55                  60

Arg Val Glu Phe Lys Asn Lys Asp Leu Ala Asp Lys Tyr Lys Asp Lys
 65                  70                  75                  80

Tyr Val Asp Val Phe Gly Ala Asn Tyr Tyr Tyr Gln Cys Tyr Phe Ser
                 85                  90                  95

Lys Lys Thr Asn Asp Ile Asn Ser His Gln Thr Asp Lys Arg Lys Thr
            100                 105                 110

Cys Met Tyr Gly Gly Val Thr Glu His Asn Ala Asn Gln Leu Asp Lys
        115                 120                 125

Tyr Arg Ser Ile Thr Val Arg Val Phe Glu Asp Gly Lys Asn Leu Leu
    130                 135                 140

Ser Phe Asp Val Gln Thr Asn Lys Lys Lys Val Thr Ala Gln Glu Leu
145                 150                 155                 160

Asp Tyr Leu Thr Arg His Tyr Leu Val Lys Asn Lys Lys Leu Tyr Glu
                165                 170                 175

Phe Asn Asn Ser Pro Tyr Glu Thr Gly Tyr Ile Lys Phe Ile Glu Asn
            180                 185                 190

Glu Asn Ser Phe Trp Tyr Asp Met Met Pro Ala Pro Gly Asp Lys Phe
        195                 200                 205

Asp Gln Ser Lys Tyr Leu Met Met Tyr Asn Asp Asn Lys Met Val Asp
    210                 215                 220

Ser Lys Asp Val Lys Ile Glu Val Tyr Leu Thr Thr Lys Lys Lys
225                 230                 235


<210> SEQ ID NO 2
<211> LENGTH: 4
<212> TYPE: PRT
<213> ORGANISM: Artificial
<220> FEATURE:
<223> OTHER INFORMATION: Modified sequence at residues No. 226 to No.
      229 in SEB

<400> SEQUENCE: 2
```

Leu Phe Ala Ala
1 4

<210> SEQ ID NO 3
<211> LENGTH: 4
<212> TYPE: PRT
<213> ORGANISM: Artificial
<220> FEATURE:
<223> OTHER INFORMATION: Modified sequence at residues No. 226 to No. 229 in SEB

<400> SEQUENCE: 3

Ala Thr Thr Gln
1 4

<210> SEQ ID NO 4
<211> LENGTH: 4
<212> TYPE: PRT
<213> ORGANISM: Artificial
<220> FEATURE:
<223> OTHER INFORMATION: Modified sequence at residues No. 226 to No. 229 in SEB

<400> SEQUENCE: 4

Lys Arg Ile Ile
1 4

<210> SEQ ID NO 5
<211> LENGTH: 10
<212> TYPE: PRT
<213> ORGANISM: Artificial
<220> FEATURE:
<223> OTHER INFORMATION: Epitope region of N23Y SEB variant

<400> SEQUENCE: 5

Ser Lys Asp Val Lys Ile Glu Val Tyr Leu
1 5 10

<210> SEQ ID NO 6
<211> LENGTH: 10
<212> TYPE: PRT
<213> ORGANISM: Artificial
<220> FEATURE:
<223> OTHER INFORMATION: Epitope region of 42-C2 SEB variant including modified sequence at residues No. 226 to No. 229

<400> SEQUENCE: 6

Ser Leu Phe Ala Ala Ile Glu Val Tyr Leu
1 5 10

<210> SEQ ID NO 7
<211> LENGTH: 10
<212> TYPE: PRT
<213> ORGANISM: Artificial
<220> FEATURE:
<223> OTHER INFORMATION: Epitope region of 42-C7 SEB variant including modified sequence at residues No. 226 to No. 229

<400> SEQUENCE: 7

Ser Ala Thr Thr Gln Ile Glu Val Tyr Leu
1 5 10

<210> SEQ ID NO 8
<211> LENGTH: 10
<212> TYPE: PRT
<213> ORGANISM: Artificial
<220> FEATURE:
<223> OTHER INFORMATION: Epitope region of 4-C1 SEB variant including -continued

```
      modified sequence at residues No. 226 to No. 229

<400> SEQUENCE: 8

Ser Lys Arg Ile Ile Ile Glu Val Tyr Leu
  1               5                  10


<210> SEQ ID NO 9
<211> LENGTH: 10
<212> TYPE: PRT
<213> ORGANISM: Artificial
<220> FEATURE:
<223> OTHER INFORMATION: Epitope region of 48-C4 SEB variant including
      modified sequence at residues No. 226 to No. 229

<400> SEQUENCE: 9

Ser Pro Gln Pro Asp Ile Glu Val Tyr Leu
  1               5                  10
```